(12) United States Patent
Schenk et al.

(10) Patent No.: US 6,521,191 B1
(45) Date of Patent: *Feb. 18, 2003

(54) PERMEATION CELL FOR IN VITRO DETERMINATION OF SKIN PERMEATION OF PHARMACEUTICAL DRUGS

(75) Inventors: Dirk Schenk, Dietramszell (DE); German Gassner, Friedberg (DE)

(73) Assignee: Novosis AG, Munich (DE)

( * ) Notice: Subject to any disclaimer, the term of this patent is extended or adjusted under 35 U.S.C. 154(b) by 77 days.

This patent is subject to a terminal disclaimer.

(21) Appl. No.: 09/611,199

(22) Filed: Jul. 6, 2000

Related U.S. Application Data

(63) Continuation-in-part of application No. 09/372,852, filed on Aug. 12, 1999, now Pat. No. 6,294,134.

(30) Foreign Application Priority Data

Jul. 7, 1999 (DE) ..................................... 299 11 790 U

(51) Int. Cl.$^7$ .................................................. B01L 3/00
(52) U.S. Cl. ........................... 422/102; 73/38; 422/101; 435/288.2; 435/297.1
(58) Field of Search ................................. 422/101, 102, 422/99; 435/288.1, 288.2, 297.5, 297.1, 304.1, 304.2, 204.1; 73/38; 64.47; 210/321.6, 321.72, 321.75; 204/415

(56) References Cited

U.S. PATENT DOCUMENTS 4,579,631 A * 4/1986 Ishikawa et al.
4,706,495 A * 11/1987 Steudle et al.
5,030,575 A * 7/1991 Stofac
6,087,157 A * 7/2000 Badylak et al.
6,294,134 B1 * 9/2001 Schenk et al.

* cited by examiner

Primary Examiner—Jan Ludlow
(74) Attorney, Agent, or Firm—Frommer Lawrence & Haug, LLP; Ronald R. Santucci

(57) ABSTRACT

A permeation cell for the in vitro determination of the permeation of pharmaceutical active ingredients through the skin, having a donor chamber (34) and an acceptor chamber (4) that is separable therefrom, a window lying between them for receiving sealingly a skin membrane and sealingly closable filling and emptying openings at both chambers, characterized in that the acceptor chamber (4) is in the form of a cylindrical vessel that is upright during operation, having a closure (8; 50; 80) at its upper end and a side window opening (6) in the region near its base, and the donor chamber (34) is in the form of a connection piece that joins onto the acceptor chamber radially and can be closed at its outer end, with the exception of its closure (8; 50; 80) the acceptor chamber (4) is inserted removably into a housing (10) that fits closely around it, which housing has, in the region of the window opening (6) of the acceptor chamber, a corresponding slightly wider opening (30), and the connection piece forming the donor chamber (34) is screwed removably onto the housing concentrically with the window opening (6). As a result, the permeation cell gains stability, it is as easy to manipulate as it is to manufacture, auxiliary means for attaching the skin membrane not being required, and the acceptor chamber has only a small dead volume. By constructing the housing (10) essentially in block form, several such permeation cells can be used next to one another in a common heating and/or stirring device.

13 Claims, 4 Drawing Sheets

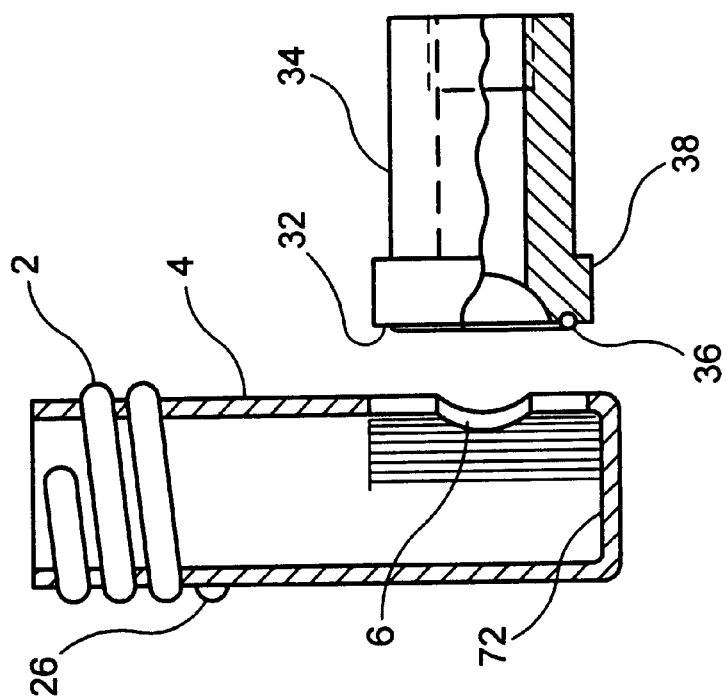
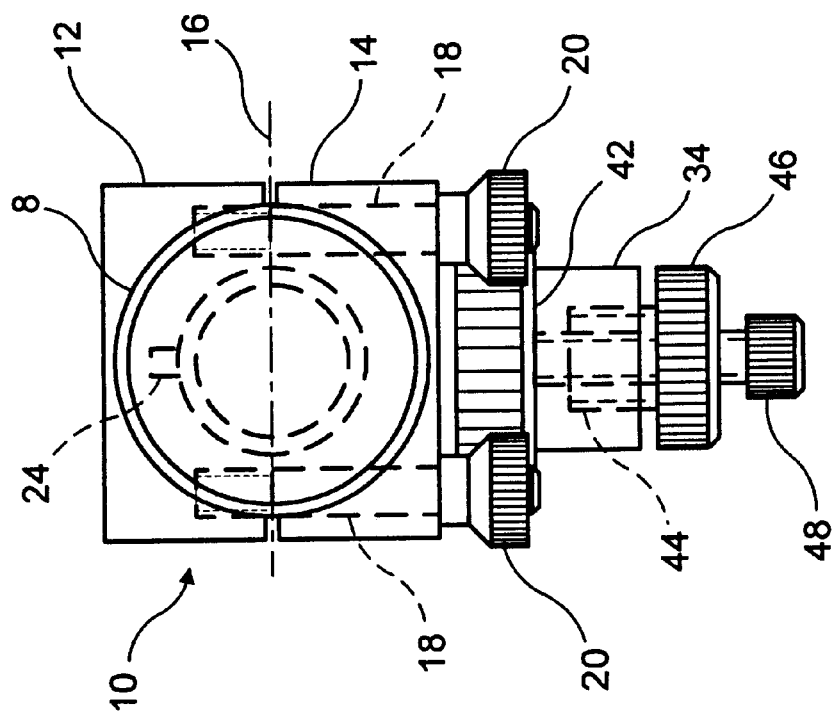
FIG. 4
FIG. 3

PERMEATION CELL FOR IN VITRO DETERMINATION OF SKIN PERMEATION OF PHARMACEUTICAL DRUGS

CROSS-REFERENCE TO RELATED APPLICATION

This application is a continuation-in-part of U.S. Ser. No. 09/372,852 filed Aug. 12, 1999 entitled "Permeation Cell for In Vitro Determination of Skin Permeation of Pharmaceutical Drugs" now U.S. Pat. No. 6,294,134.

The invention relates to a permeation cell according to the preamble of patent claim 1.

Such a permeation cell is known in that form as a so-called Franz cell, and it is customary for a bell-shaped donor chamber to be placeable on an upright pot-shaped acceptor chamber with a flat stainless steel ring and a sealing ring being placed between them, the donor chamber having a filling tube that ends inside it in a bell and the acceptor chamber having a tube that emerges upwards from the side at an angle for taking samples manually. A membrane in the form of a skin specimen must be stuck onto the stainless steel ring and then the above-mentioned parts of the Franz cell must be stuck sealingly together. Such a construction is relatively complicated to manipulate and also has the disadvantage that, as a result of degassing of the acceptor medium, gas bubbles collect on the underside of the membrane, as a result of which the diffusion of the active ingredient from the donor region is disturbed and substantially fluctuating permeation results are produced.

A permeation cell has already been proposed in which the membrane extends vertically during operation and the acceptor chamber can be inserted by means of two connection pieces into a so-called HPLC (high pressure liquid chromatography) apparatus or the like for automatic evaluation. In addition, inside the acceptor chamber there is a magnetic stirring rod that can be rotatably driven by means of an external magnetic stirring device. In that construction, however, an irregularly shaped donor chamber is attachable around a window opening on the likewise irregularly shaped acceptor chamber by means of a frame and a locking screw, resulting in a construction that is complicated and in turn difficult to manipulate. Moreover, the acceptor chamber has a relatively large dead volume, so that controllable flow conditions at the membrane cannot be obtained without difficulty.

On that basis, the problem underlying the invention is so to construct a permeation cell having the features of the preamble that it is as simple to construct as it is to manipulate and avoids the collection of gas bubbles at the membrane. It should also be possible to obtain predictable uniform flow conditions at the membrane.

The problem is solved essentially by the characterising features of claim 1. In addition, the dependent claims give advantageous construction options.

The construction in question of the acceptor chamber in the form of an upright cylindrical vessel having a side window opening in the region near its base, the enclosure of the acceptor chamber in a housing that fits closely around it and the construction of the donor chamber in the form of a connection piece that can be screwed onto the cylindrical acceptor chamber radially thereto yield a permeation cell having a vertical membrane and low dead volumes in both chambers that is as easy to manufacture as it is to use. Moreover, the construction of the housing in the form of an essentially parallelipipedal block according to claim 10 facilitates the economical use of several such permeation cells next to one another in a hot water bath with a stirring plate or the like.

BRIEF DESCRIPTION OF THE DRAWINGS

An embodiment of the invention that is currently preferred together with a variant will be explained hereinafter in greater detail with reference to the figures, in which:

FIG. 3 is a plan view of the same permeation cell;

FIG. 4 is a diagram of the donor and acceptor chambers of the same permeation cell, largely cut away;

FIG. 6 is a section through a further closure of the acceptor chamber to enable continuous removal of samples for an HPLC apparatus or the like.

Figure 2:
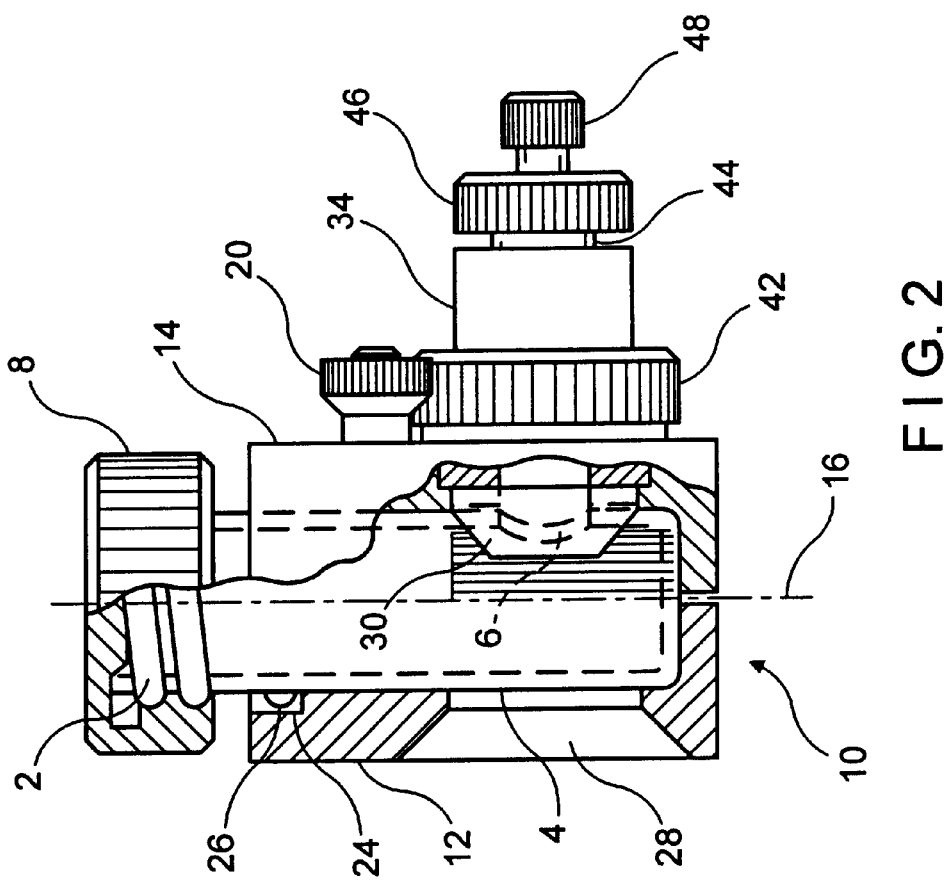
FIG. 2 is a side view of the same permeation cell from a viewing angle at right angles to the viewing angle of FIG. 1, partially cut away.

As can be seen from FIGS. 2 and 4 in particular, the permeation cell in question has a cylindrical acceptor chamber 4 that is closed at the bottom, is provided at its upper end region with an external thread 2 and is usually made of glass. In its lower portion, the acceptor chamber 4 has an essentially circular side window opening 6, on the rim of which the rim of the skin membrane (not shown) comes to rest from the outside, during use, in a manner described further. The closure of the acceptor chamber 4 is formed by an imperforate screw top 8 that has an internal thread that matches the thread 2 of the acceptor chamber.

In the assembled state of the permeation cell shown, the acceptor chamber 4 is surrounded by a two-part, block-like housing 10 comprising the two housing parts 12 and 14, which at least approximately meet one another along a longitudinal centre plane 16 of the acceptor chamber 4, which longitudinal centre plane is perpendicular to the axis of the window opening 6, and are held together by two screw bolts 18 on the housing portion 12 and by two knurled nuts 20 placed on the housing portion 14 after it has been positioned. The resulting housing 10 comprises a bore 22 which is ground, at least in its lower section, together with the outer surface of the acceptor chamber 4, so that they match, in order to fix the acceptor chamber precisely inside the housing 10. The angular position of the acceptor chamber 4 relative to the housing 10 is determined by a projection 26 projecting into a corresponding recess 24 in the housing portion 12.

Whilst the housing portion 12 has a viewing opening 28 concentric with the axis of the window opening 6 of the so secured acceptor chamber 4, the housing portion 14 has opposite thereto, around the window opening 6, an opening 30 which is large enough to receive the skin membrane inside it contact-free.

As can also be seen from FIGS. 2 and 4, inside the opening 30 there comes to rest on the acceptor chamber 4, or more precisely on the skin membrane resting thereon, the end face rim 32 of a substantially cylindrical donor chamber 34, into which end face rim there is inserted an O-ring 36 for sealing purposes. To that end, the donor chamber 34 has an outwardly projecting flange 38 and the housing portion 14 has a collar 40 that is provided with an external thread, onto which collar there can be screwed a union nut 42 which presses the flange 38 against the acceptor chamber 4. As a result of that screw connection in conjunction with the O-ring 36, the donor chamber 34 is held tightly against the acceptor chamber 4, the skin membrane being enclosed equally tightly without the need for adhesion.

Inserted tightly in the outer end of the donor chamber 34 is a screw nipple 44, onto which a screw top 46 can be screwed as closure of the donor chamber 34. The screw top 46 comprises a bleed valve 48 in the form of a central screw plug.

To use the permeation cell described thus far, the procedure is as follows: The housing portion 12 is placed on a table with its viewing opening 28 facing down, and the acceptor chamber 4 is then inserted into the housing portion 12. A circular skin specimen having a diameter that exceeds that of the window opening 6 by about 4 mm is then placed concentrically on the window opening 6, and, if the permeation of an active ingredient through the skin from a transdermal therapeutic system (TTS) is to be studied, firstly a sample of such a system is applied to the outside of the skin specimen. The housing portion 14 is then positioned and connected to the housing portion 12 by means of the knurled nuts 20. The donor chamber 34 is then placed on the skin specimen inside the opening 30 of the housing portion 14 and is connected to the housing 10 by means of the union nut 42. Correct assembly of the cell can be monitored through the viewing opening 28.

After the cell has been positioned upright, the intended acceptor solution is introduced into the acceptor chamber 4, after which the acceptor chamber is closed by means of the screw top 8. It is possible, by varying the level to which the acceptor chamber is filled, to take into account different permeation capacities of the active ingredient to be studied. In the case of active ingredients that permeate strongly, advantageously the sink conditions are optimised by maximum filling and in the case of low permeation capacity the detection sensitivity is optimised by a minimal level of filling.

If the permeation of an active ingredient through the skin is to be studied from a solution instead of from a transdermal therapeutic system, instead of applying an active ingredient to the skin specimen, after the cell has been assembled and is still resting on the viewing opening 28 the donor chamber 34 is filled to about the rim with the active ingredient solution in question, and then, with the bleed valve 48 open, the screw top 46 is put on. Excess active ingredient solution exits through the bleed valve 48, which is then closed.

Figure 1:
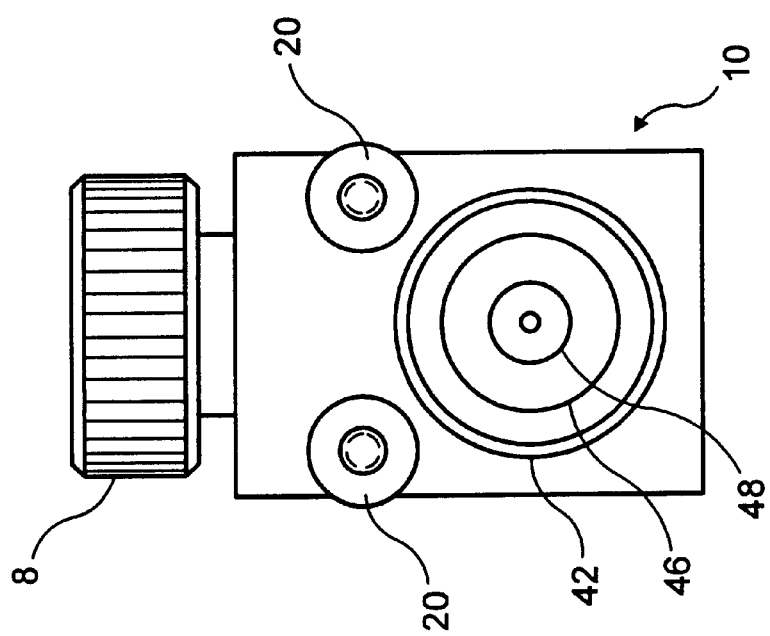
FIG. 1 is a side view of the permeation cell in question, viewed from the end face of its cylindrical donor chamber.
Figure 5:
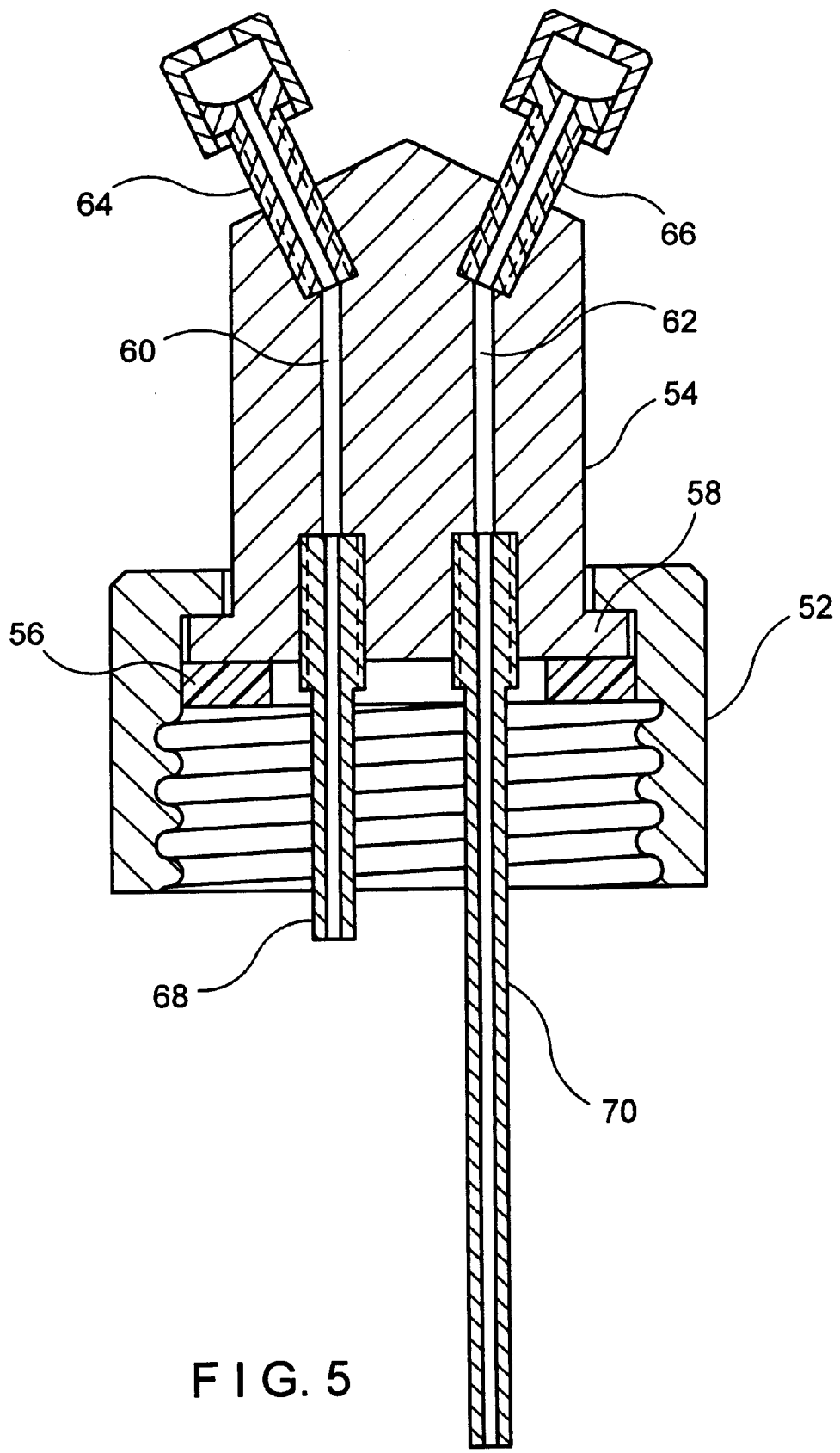
FIG. 5 is a section through a different closure of the acceptor chamber of an otherwise identical permeation cell that enables it to be connected to an HPLC apparatus.

If the permeation cell in question is to form the sample-loading device of an HPLC apparatus, there is used instead of the screw top 8 from FIGS. 1 and 2 a screw top 50 according to FIG. 5. This consists essentially of a union nut 52 that matches the thread 2 of the acceptor chamber 4 and an insert 54 which can be attached tightly to the acceptor chamber 4 by the union nut and which carries on its internal end a flange 58 that comes to rest sealingly by way of a sealing ring 56 on the end face of the acceptor chamber 4. The insert 54 comprises two channels 60 and 62 that pass through it axially, which are widened at both ends. Screwed into the outer widened portions are two connection pieces 64 and 66, and screwed into the inner widened portions are two capillary tubes 68 and 70. Whilst the capillary tube 68 that serves as the inlet for the acceptor solution ends a short way below the insert 54, the capillary tube 70 that serves as outlet projects further down, for example to about 15 mm above the cell floor 72 (FIG. 4), in order to determine by this means the level of filling of the acceptor fluid in the acceptor chamber. Through the viewing window 28 (FIG. 2) it is possible to monitor the acceptor solution dropping in from the capillary tube 68.

Figure 6:
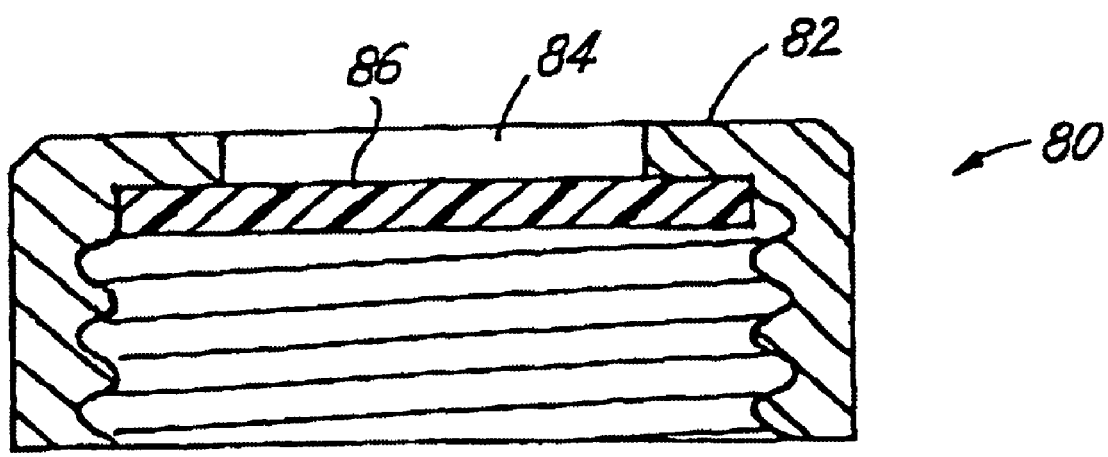

FIG. 6 shows a further closure 80 for the acceptor chamber 4 that enables samples to be taken continuously therefrom. The closure 80 consists of a screw top similar to the screw top 8 of FIGS. 1 and 2 having a central opening 84 only in its floor 82, at which opening an inserted septum 86 is exposed. The septum 86 can be made, for example, of polytetrafluoroethylene-coated silicone rubber and simultaneously forms the sealing of the screw top on the rim of the acceptor chamber 4.

Such a closure is used, for example, when the permeation cell is being used with a large number of further cells in an automatic sample-taking apparatus. In that case, for cyclic sampling a hollow needle is passed through the septum 86 into the acceptor chamber 4, and after removal of the needle the septum 86 closes again each time.

The block-like housing 10 provides the described permeation cell with stability. Moreover, it facilitates cell assembly with insertion of the skin specimen, for which purpose auxiliary means, such as, for example, adhesive strips, are not required. Finally, when it is made of a magnetically neutral heat conductor, such as a light metal, it yields, by means of an external heating device, such as, for example a hot water bath, good controllable heat transmission to the cell without preventing the use of a magnetic stirring device. Alternatively, the housing 10 may itself also comprise electrical heating means for the acceptor chamber 4, for example in the form of a heating film adhesively secured to the acceptor chamber, which, when the cell is assembled, comes into contact with electrical contacts of the housing (not shown). In the case of such electrical heating, the housing 10 is advantageously made of a heat insulating material, such as, for example, polyvinyl difluoride (PVDF), which can moreover be machined down easily to a smooth surface.

The temperature set in the acceptor chamber 4 can be regulated by means of a temperature sensor (not shown) introduced into the acceptor chamber through the screw top 8 or 50. If desired, several such cells can be used next to one another, to save space, in a common heating and/or stirring device.

What is claimed is:

1. A permeation cell for the in vitro determination of the permeation of pharmaceutical active ingredients through the skin, comprising a donor chamber (34) and an acceptor chamber (4) that is separable therefrom, a window lying between said donor and acceptor chambers for sealingly receiving a skin membrane and sealingly closable filling and emptying openings in both chambers, wherein the acceptor chamber (4) is in the form of a cylindrical vessel that is upright during operation, having a closure (8; 50; 80) at its upper end and a side window opening (6) in the region near its base, and the donor chamber (34) is in the form of a connection piece that joins onto the acceptor chamber radially and can be closed at is outer end, with the exception of said closure (8; 50; 80) the acceptor chamber (4) is removably inserted into a housing (10) that closely fits around it, which housing has, in the region of the window opening (6) of the acceptor chamber, a corresponding slightly wider opening (30), and the connection piece forming the donor chamber (34) is removably screwed onto the housing (10) concentrically with the window opening (6).

2. The permeation cell according to claim 1, wherein the connection piece forming the donor chamber (34) carries on an end face of said connection piece an O-ring (36) that comes to rest on the rim of the skin membrane.

3. The permeation cell according to claim 1, wherein the connection piece forming the donor chamber (34) can be screwed onto the housing (10) by a union nut (42).

4. The permeation cell according to claim 1, further comprising a closure (46) coupled to said donor chamber (34) and having a bleed valve (48).

5. The permeation cell according to claim 1, wherein the closure (50) of the acceptor chamber (4) has inlet and outlet channels (60, 62), separate from one another, having connection means (64, 66) on the outside for insertion into a HPLC apparatus.

6. The permeation cell according to claim 5, wherein the closure (50) has on the inside capillary tubes (68, 70) that join onto the respective inlet and outlet channels (60, 62).

7. The permeation cell according to claim 5, wherein the closure (50) consists essentially of a union nut (52) that can be screwed onto the acceptor chamber (4) and all insert (54) that is held by the nut and contains the inlet and outlet channels (60, 62) and wherein an cad face of said insert (54) can be sealingly pressed against the acceptor chamber (4) by the union nut (52).

8. The permeation cell according to claim 1, wherein the closure (80) consists of a screw top at which a septum (86) that can be pierced by a hollow needle is exposed.

9. The permeation cell according to claim 1, wherein the housing (10) is divided along a longitudinal center plane (16) of a bore (22) that receives the acceptor chamber (4) inside it, which longitudinal center plane is perpendicular to the center axis of said wider opening (30) in the housing.

10. The permeation cell according to claim 9, wherein the bore (22) and the outer surface of the acceptor chamber (4) at least in the region of the window opening (6) are ground so that they match one another.

11. The permeation cell according to claim 1, wherein the housing (10) is in the form of an essentially parallelipipedal block.

12. The permeation cell according to claim 1, wherein the housing (10) is made of plastics or of metal.

13. The permeation cell according to claim 1, wherein the housing (10) comprises or is adapted to receive an electrical heating element.

* * * * *